United States Patent
Höfel

(10) Patent No.: US 11,492,308 B2
(45) Date of Patent: Nov. 8, 2022

(54) METHOD AND APPARATUS FOR THE PRODUCTION OF ETHYLENE

(71) Applicant: LINDE GmbH, Pullach (DE)

(72) Inventor: Torben Höfel, Munich (DE)

(73) Assignee: LINDE GmbH, Pullach (DE)

( * ) Notice: Subject to any disclaimer, the term of this patent is extended or adjusted under 35 U.S.C. 154(b) by 0 days.

(21) Appl. No.: 17/285,619

(22) PCT Filed: Oct. 17, 2019

(86) PCT No.: PCT/EP2019/078303
§ 371 (c)(1),
(2) Date: Apr. 15, 2021

(87) PCT Pub. No.: WO2020/079199
PCT Pub. Date: Apr. 23, 2020

(65) Prior Publication Data
US 2021/0395168 A1    Dec. 23, 2021

(30) Foreign Application Priority Data
Oct. 18, 2018   (EP) .................................... 18201329

(51) Int. Cl.
*C07C 5/327*   (2006.01)
*C07C 7/00*    (2006.01)
(52) U.S. Cl.
CPC .............. *C07C 5/327* (2013.01); *C07C 7/005* (2013.01)
(58) Field of Classification Search
CPC ........... C07C 5/327; C07C 7/005; C07C 4/04; C07C 7/04
See application file for complete search history.

(56) References Cited

U.S. PATENT DOCUMENTS

2020/0385642 A1* 12/2020 Fickel .................... C10G 47/18

OTHER PUBLICATIONS

PCT/EP2019/078303 International Search Report dated Dec. 12, 2019, 2 pages.

(Continued)

*Primary Examiner* — Thuan D Dang
(74) *Attorney, Agent, or Firm* — Lathrop GPM LLP

(57) ABSTRACT

A process (100, 200, 300) for the production of ethylene is proposed in which a first feed gas (A) and a second feed gas (B) are fed to a reactor (1) and processed therein by vapour cracking to obtain a product mixture (C), the first feed gas (A) comprising more than 90 weight percent saturated hydrocarbons and more than 80 weight percent ethane, and wherein the product mixture (C) or a part thereof is subjected to a treatment (2, 3, 4) and the resulting mixture (F) or a part thereof is subjected to a separation (10) to obtain a resulting mixture (F) containing hydrogen, methane, ethane, ethylene and hydrocarbons having three, four and at least five carbon atoms. The separation (10) being provided in that it comprises an ethylene separation step (7) to which at least the ethane, the ethylene and the hydrocarbons having three carbon atoms from the succeeding mixture (F) or a part thereof are fed unseparated from each other in a common separation insert (S, V, X), in which in the ethylene separation step (7) a light fraction (K) containing more than 95 mole percent ethylene is fed, and a heavy fraction (T, W, Y) containing at least a portion of the ethane from the separation insert (S, V, X) and at least 15% by weight of the hydrocarbons having three and four carbon atoms from the separation insert (S, V, X), and wherein the heavy separation product (T, W, Y) from the ethylene separation step (7) or a portion thereof is used as part or to form the second feed gas (B). A corresponding annex is also the subject of this invention.

15 Claims, 2 Drawing Sheets

(56) References Cited

OTHER PUBLICATIONS

PCT/EP2019/078303 International Preliminary Report on Patentability dated Apr. 14, 2021, 6 pages.
Zimmermann, et al., Ethylene, Wiley-VCH Verlag GmbH & Co. KGaA, Weinheim, 2009, 66 pages.

* cited by examiner

METHOD AND APPARATUS FOR THE PRODUCTION OF ETHYLENE

The present invention relates to a process for the production of ethylene and a corresponding apparatus according to the preambles of the independent patent claims.

PRIOR ART

Olefins such as ethylene or propylene, but also diolefins such as butadiene and aromatics can be produced from paraffins by steam cracking. Such procedures have been known for a long time. For details reference is made to technical literature such as the article "Ethylene" in Ullmann's Encyclopedia of Industrial Chemistry, Online Edition, 15 Apr. 2007, DOI 10.1002/14356007.a10_045.pub2.

In steam cracking, a so-called cracked gas is obtained which, in addition to the target products, contains unreacted hydrocarbons and unwanted by-products. This cracked gas is first subjected to a treatment in known processes before it is fed to a fractionation or separation for the recovery of different hydrocarbons or fractions. Details are described in the article cited, in particular in Section 5.3.2.1, "Front-End Section" and Section 5.3.2.2, "Hydrocarbon Fractionation Section".

A corresponding treatment comprises in particular a so-called sour gas removal, in which components such as carbon dioxide, hydrogen sulphide and mercaptans are separated from the cracked gas. The cracked gas is typically compressed before and after a corresponding treatment. For example, the cracked gas can be withdrawn from a so-called raw gas compressor at an intermediate pressure level, subjected to sour gas removal, and then further compressed in the raw gas compressor.

Sometimes it is desirable to convert ethane-rich feedstocks into ethylene by steam cracking while forming as small quantities of by-products as possible. In this context, in addition to unreacted ethane, hydrocarbons with three and four carbon atoms formed during steam cracking are typically returned to the reactor(s) used. In order to avoid an individual hydrogenation of these recycled fractions, the entire cracked gas can be hydrogenated in the course of treatment (so-called raw gas hydrogenation).

Since the recirculated hydrocarbons with three and four carbon atoms typically account for a small proportion of the total feed to be converted, these hydrocarbons are typically cracked together with the freshly fed or recirculated ethane. In other words, there is no need to provide separate units for steam cracking.

FIG. 1 shows a corresponding procedure in the form of a schematic flowchart and is explained in detail below with reference to FIG. 1. However, as indicated there, this procedure involves a separation which is more burdensome than would be necessary for the purposes explained.

Against this background, this invention has the task of improving an appropriate method and making it simpler in terms of separation technology, thereby reducing investment and/or operating costs.

DISCLOSURE OF THE INVENTION

Against this background, the present invention proposes a method for the production of ethylene and a corresponding apparatus according to the preambles of the respective independent patent claims. Preferred embodiments are the subject of the dependent claims as well as the following description.

Before explaining the advantages of the present invention, some terms used in the description of the invention are defined in more detail below.

Component mixtures can be rich or poor in one or more components in the language used here, wherein the term "rich" can stand for a content of at least 75%, 80%, 90%, 95% or 99% and the term "poor" for a content of at most 25%, 20%, 10%, 5% or 1% on a molar, weight or volume basis. Component mixtures can also be enriched or depleted of one or more components in the language used here, wherein these terms refer to a corresponding content in another component mixture using which the component mixture under consideration was formed. The component mixture under consideration is "enriched" when it has at least 1.5 times, 2 times, 5 times, 10 times, 100 times or 1,000 times the content of the designated component(s) and "depleted" when it has at most 0.75 times, 0.5 times, 0.1 times, 0.01 times or 0.001 times the content of the designated component(s). A component mixture "predominantly" containing one or more components is especially rich in this or these components in the sense just explained.

If there is talk here of a component mixture being "formed" using another component mixture, this means that the component mixture under consideration contains at least some of the components contained in or formed by the other component mixture. Forming a component mixture from another may include, for example, branching off a part of the component mixture, admixing one or more other components or component mixtures, chemical or physical conversion of at least some components, and heating, cooling, evaporation, condensing, etc. A "forming" of a component mixture from another component mixture can also only include the provision of the other component mixture in a suitable form, for example in a container or a pipe.

The present application uses the terms "pressure level" and "temperature level" to characterise pressures and temperatures, which are intended to express that corresponding pressures and temperatures in a corresponding plant do not have to be used in the form of exact pressure or temperature values. However, such pressures and temperatures typically lie within in certain ranges, such as ±1%, 5%, 10%, 20% or 25% around a median value. Corresponding pressure levels and temperature levels can lie in disjunctive ranges or in overlapping ranges. The same pressure level may still be present, for example, if unavoidable pressure losses occur. The same applies to temperature levels. The pressure levels given here in bar are absolute pressures.

Advantages of the Invention

This invention proposes a method for the production of ethylene in which a first feed gas (fresh feed gas) and a second feed gas (recycled feed gas) are fed into a reactor, where they are processed by steam cracking to obtain a product mixture (cracked gas). The first feed gas can consist in particular of so-called raw ethane with customary specifications and can be supplied in particular from the plant boundary. The first feed gas contains more than 90% by weight, in particular more than 95% by weight, of saturated hydrocarbons and more than 80% by weight, in particular more than 85%, 90% or 95% by weight, of ethane. A content of propane in the first feed gas is in particular up to 15 weight percent, for example up to 10 or up to 5 weight percent.

The first feed gas is in particular poor in or (essentially) free of heavier hydrocarbons, the content of which may in particular be a maximum of 5 percent by weight or 1 percent by weight. The term "heavier hydrocarbons" here refers in particular to hydrocarbons with four or more carbon atoms.

The first feed gas may contain up to 5 percent methane by weight. In particular, it is free of or at least poor in carbon dioxide and other trace components. All explanations concerning a "feed gas" refer to the fresh feed directly at the reactor, i.e. a corresponding feed gas may already have been pre-treated, e.g. depleted of 002.

The steam cracking in the context of the present invention is carried out in particular to avoid the excessive formation of by-products with a medium or low ethane conversion of for example 65% or less, 60% or less, 55% or less, 50% or less or 45% or less and 10% or more, 20% or more or 30% or more. Therefore, comparatively large amounts of ethane remain in the product mixture. Further parameter settings for steam cracking can be made by a specialist as required. In particular, appropriate settings such as steam dilution and reactor pressure are selected in such a way that a comparatively large amount of ethylene is produced from the converted ethane and comparatively few hydrocarbons with three or more carbon atoms are produced.

If the specification speaks about "one" reactor in each case, it goes without saying that instead of just one reactor, several reactors can also be used in serial or parallel operation, to which one or more corresponding feed gases can then be fed. Several of these reactors ("cracking furnaces") can be operated in the same or different ways.

In the present invention, the product mixture which is removed from the reactor, or a part thereof, is subjected to a treatment to obtain a subsequent mixture containing hydrogen, methane, ethane, ethylene and hydrocarbons containing three, four and at least five carbon atoms, and in particular consisting (essentially) of these components. The treatment can be carried out in the usual way (see above). In particular, such treatment may include hydrogenation of acetylene and partial hydrogenation of, in particular, mono- and polyunsaturated hydrocarbons containing three carbon atoms in order to avoid corresponding hydrogenation during the recycling of components. A correspondingly formed subsequent mixture or part thereof is then subjected to a separation within the scope of the present invention.

The present invention is characterised by the fact that the separation comprises an ethylene separation step to which at least the ethane, the ethylene and the hydrocarbons with three carbon atoms from the subsequent mixture or a part thereof are fed unseparated from each other in a common separation feed. In contrast to known ethylene separation steps, which in the state of the art typically consist essentially of a separation of ethane and ethylene from each other (in a so-called C2 splitter), the present invention therefore separates ethylene in a corresponding separation step from a remaining fraction which contains not only ethane but also substantial parts of the heavier hydrocarbons from the product mixture. Since, in the context of the present invention, comparatively small quantities of hydrocarbons with three carbon atoms are formed overall due to the composition of the first feed gas and are thus present in the product mixture, the remaining fraction comprises in particular still more than 50 percent by weight, in particular more than 60 percent by weight, more than 70 percent by weight, more than 80 percent by weight or more than 85 percent by weight, and in particular up to 95 percent by weight or up to 90 percent by weight of ethane and otherwise heavier hydrocarbons, at least those with three carbon atoms. However, the heavier hydrocarbons are not separated upstream of the ethylene separation step as in conventional processes. This applies at least to hydrocarbons with three carbon atoms, as indicated below.

Depending on the design of the method in accordance with the invention, the ethylene separation step can also be fed with hydrocarbons with four and possibly five carbon atoms, as explained in detail below. The ethylene separated here or a light fraction from the ethylene separation step can be exported as an ethylene product from the method. An essential aspect of this invention is the inseparable feeding of the abovementioned components into the ethylene separation step. This facilitates upstream separation and contributes to a reduction in separation effort.

If it is stated here that at least ethane, ethylene and hydrocarbons with three carbon atoms from the subsequent mixture or a part thereof are fed "unseparated" to the ethylene separation step, this is to be understood that these components are carried forward at least partly in a continuous material flow (from which, however, a part or certain components, including the hydrocarbons with three carbon atoms, can be separated) from the reactor to the ethylene separation step. Depending on the specific design of the method, the separation feed for the ethylene separation step may also include, in particular, hydrocarbons with four carbon atoms or hydrocarbons with four and at least five carbon atoms, which are thus also fed unseparated to the ethylene separation step.

In the ethylene separation step, the abovementioned light fraction containing more than 95 mole percent, in particular more than 99 mole percent, of ethylene and in particular (essentially) consisting of ethylene, and a heavy fraction containing at least part of the ethane from the separation feed (S, V, X) and at least 15 weight percent of the hydrocarbons containing three and four carbon atoms (optionally also heavier hydrocarbons) are formed. In particular, the heavy fraction may contain more than 20 percent by weight, more than 30 percent by weight, more than 40 percent by weight, more than 50 percent by weight, more than 60 percent by weight, more than 70 percent by weight, more than 80 percent by weight or more than 90 percent by weight of hydrocarbons containing three and four carbon atoms (or heavier hydrocarbons, as the case may be), the latter values being usable to specify upper limits for corresponding ranges as well. The values result from the comparatively high dilution of these components with ethane. The heavy fraction can (essentially) be free of ethylene. The heavy fraction from the ethylene separation step or part thereof (directly or with separation of any heavier components contained) is used to form the second feed gas.

In order to reduce the separation effort, the present invention may, in particular, be used for "soft" or "fuzzy" deethanisation, in which a fraction containing ethane and ethylene is not formed, as is known from the state of the art, which is (essentially) free of other components, in particular heavier components. This is combined with demethanisation. However, only demethanisation can also take place.

Thus, in the present invention, the separation feed to be fed to the ethylene separation step can be formed using a first pre-separation step and a second pre-separation step, the subsequent mixture or its part subjected to separation being fed to the first pre-separation step in unchanged composition, a light fraction and a heavy fraction being formed in the first pre-separation step, wherein the light fraction from the first pre-separation step or a part thereof is fed to the second pre-separation step, wherein in the second pre-separation step a light fraction and a heavy fraction are formed, and wherein the heavy fraction from the second pre-separation step or a part thereof is used as the separation feed or a part thereof which is fed to the ethylene separation step. The first pre-separation step corresponds to the already mentioned soft deethanization, the second pre-separation step to a demethanization (corresponding to the usual).

The separation limits in the soft deethanization used according to the invention can be set differently. In a first alternative, the light fraction from the first pre-separation step may contain less than 1 mole percent of hydrocarbons with four and at least five carbon atoms and in the remainder methane, ethane, ethylene and hydrocarbons with three carbon atoms. In this case, the heavy fraction from the first pre-separation step may contain less than 1 mole percent hydrogen, methane and ethylene and in the remainder ethane, hydrocarbons with three, four and at least five carbon atoms. The task of this separation step in the first alternative is in particular to separate ethylene and hydrocarbons with four and at least five carbon atoms, whereas hydrocarbons with three carbon atoms are contained in both fractions. In this first alternative, the light fraction from the second pre-separation step, i.e. demethanisation, also contains a total of more than 99 mole percent methane and hydrogen, and the heavy fraction from the second pre-separation step contains a total of less than 1 mole percent methane and hydrogen and in the remainder ethane, ethylene and hydrocarbons with three carbon atoms.

In a second alternative, the separation limit in soft deethanisation may be set such that the light fraction from the first pre-separation step contains less than 1 mole percent in total of hydrocarbons having at least five carbon atoms and in the remainder methane, ethane, ethylene and hydrocarbons having three and four carbon atoms, and the heavy fraction from the first pre-separation step contains less than 1 mole percent in total of hydrogen, methane and ethylene and in the remainder ethane and hydrocarbons having three, four and at least five carbon atoms. The task of this separation step in the second alternative is in particular the separation of ethylene and hydrocarbons with at least five carbon atoms. In this second alternative, the light fraction from the second pre-separation step, i.e. demethanization, basically contains more than 99 mole percent methane and hydrogen as above. The heavy fraction from the second pre-separation step also contains a total of less than 1 mole percent methane and hydrogen, but in the remainder ethane, ethylene and hydrocarbons with three and four carbon atoms.

In both of the alternatives described above, the heavy fraction from the first pre-separation step or part of it can be subjected to a further separation step in which a light fraction and a heavy fraction are formed. The light fraction contains either less than 1 mole percent of hydrocarbons containing at least six carbon atoms and in the remainder hydrocarbons containing three, four and five carbon atoms or less than 1 mole percent of hydrocarbons containing at least five carbon atoms and in the remainder hydrocarbons containing three and four carbon atoms. In this case, the heavy fraction may contain either, according to the first alternative for the composition of the light fraction just indicated, predominantly or exclusively hydrocarbons containing at least six carbon atoms or, according to the second alternative for the composition of the light fraction just indicated, predominantly or exclusively hydrocarbons containing at least five carbon atoms.

The task of the separation step last explained is to generate a suitable recycle. At least hydrocarbons with six carbon atoms should be removed, possibly also hydrocarbons with five carbon atoms. In the latter case, this further separation step is therefore a typical debutanization step, as is generally known from the state of the art.

According to a third alternative, however, the separation feed fed to the ethylene separation step can also be formed using only a single pre-separation step to which the subsequent mixture of unchanged composition is fed. This also involves demethanisation. In this single pre-separation step, a light fraction containing more than 99 mole percent methane and hydrogen is formed. Due to the addition of hydrocarbons, a heavy fraction formed in the single pre-separation step contains less than 1 mole percent of methane and hydrogen but the remainder is ethane, ethylene and hydrocarbons containing three, four and at least five carbon atoms. This heavy fraction from the single pre-separation step or part thereof shall be used as the separation feed or part of the separation insert fed to the ethylene separation step.

If a single pre-separation step is used instead of a first and a second pre-separation step, as in the third alternative just explained, at least part of the heavy fraction remaining after the ethylene separation step is advantageously fed to a further separation step in which a light fraction and a heavy fraction are formed. The light fraction contains either less than 1 mole percent of hydrocarbons containing at least six carbon atoms and the remainder hydrocarbons containing three, four and five carbon atoms or less than 1 mole percent of hydrocarbons containing at least five carbon atoms and the remainder hydrocarbons containing three and four carbon atoms. In this case, the heavy fraction may contain either, according to the first alternative for the composition of the light fraction just indicated, predominantly or exclusively hydrocarbons containing at least six carbon atoms or, according to the second alternative for the composition of the light fraction just indicated, predominantly or exclusively hydrocarbons containing at least five carbon atoms.

Here, too, the task of the separation step last explained is to generate a suitable recycling method in which at least hydrocarbons with six carbon atoms, and possibly also hydrocarbons with five carbon atoms, are removed. This further separation step in the latter case is a typical debutanization step, as it is generally known from the state of the art.

It is understood that in each of the cases in which hydrocarbons with at least six carbon atoms are transferred into a fraction, as described above and below, these hydrocarbons are contained in the product mixture.

In all cases where a separation step previously referred to as a "further separation step" is used, its light fraction or part thereof is used to form the second feed gas, as it is poor in or free of hydrocarbons with six and possibly more carbon atoms and possibly also five carbon atoms and contains hydrocarbons which are suitable for recirculation in steam cracking. This is particularly the case if the treatment of the cracked gas, which has been explained several times, involves hydrogenation. The light fraction from the further separation step can be combined with the heavy fraction from the ethylene separation step in the first and second alternatives.

The heavy fraction from the further separation step, on the other hand, is typically carried out from the method together with a fraction from the treatment which contains hydrocarbons with at least five or at least six carbon atoms. This is what is known as pyrolysis gasoline, which can be used in a manner known per se, for example as a fuel or to produce aromatics.

The three alternatives of the present invention described above (with first and second pre-separation steps with different separation limits in the first pre-separation step and the alternative without the first pre-separation step) each have different advantages with regard to production and operating costs, which are summarised below. The expert therefore selects the alternatives described above according to the requirements.

Under the first alternative, a reduction of 3.6 MW in the required shaft power, 6.3 MW in the second alternative and 6.9 MW in the third alternative can be achieved (here and below the "reduction" refers to a non-inventional method as illustrated in FIG. 1). This is due to the soft or omitted separation in the deethanizer. There is also a reduction in the amount of low-pressure steam required (expressed in the amount of energy required to provide it) by 10.8 MW (first alternative), 13 MW (second alternative) and 16 MW (third alternative 3), respectively. This can be attributed to the reduced or eliminated heating power in deethanisation.

In the second alternative, deethanisation can take place at a significantly lower pressure than in the first alternative and in the non-inventive design, which results not only in lower compressor capacity but also in material savings. The same applies to the number of plates in deethanisation, which can also be reduced in the second alternative. In the third alternative, it may be advantageous to equip debutanization with an additional low-pressure absorber.

In the third alternative, a reduction of a plate fin heat exchanger area by approx. 600 kW/K is possible, in particular due to the elimination of deethanisation. A reduction in a block-in-shell heat exchanger area is approx. 750 kW/K in the first alternative, approx. 1 450 kW/K in the second alternative and approx. 1 800 kW/K in the third alternative. A shell and tube heat exchanger area can be reduced by approx. 2 600 kW/K in the first alternative, approx. 4 300 kW/K in the second alternative and approx. 5 700 kW/K in the third alternative.

This invention also covers an apparatus for the production of ethylene, for which reference is made to the corresponding independent claim. Reference is made to the above explanations regarding the features and advantages of such a plant, which may in particular be designed to carry out a method as it was explained in detail previously in various forms.

The invention is explained in more detail below with reference to the attached drawings, which illustrate embodiments of the present invention in comparison with an embodiment not conforming to the invention.

SHORT DESCRIPTION OF THE DRAWINGS

DETAILED DESCRIPTION OF THE DRAWINGS

Figure 1:
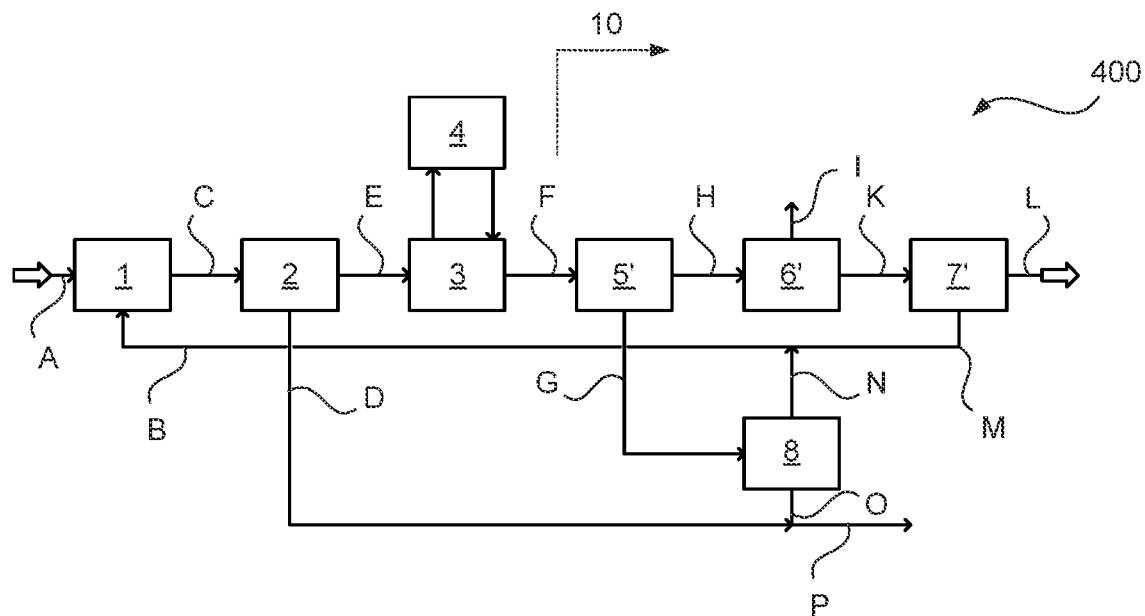
FIG. 1 illustrates a procedure according to a design form that is not in keeping with the invention.

In the following figures, structural or functional elements corresponding to each other are indicated with identical reference numerals. The same applies to material flows marked with capital letters. It is understood in each case that the corresponding components can comprise different structural designs or that the corresponding material flows can be composed differently in some cases without being designated differently in each case.

In the following, methods are described according to non-inventive and inventive embodiments. However, the corresponding explanations concern devices for carrying out such procedures in the same way. Therefore, if reference is made in the following to method steps, the corresponding explanations apply in the same way to apparatus components intended for the implementation of corresponding method steps.

FIG. 1 illustrates a method for the production of ethylene according to an embodiment not in accordance with the invention in the form of a schematic process diagram and is designated 400 in total.

In method 400, a feed gas A is fed to reactor 1 from the plant boundary (as illustrated by an arrow symbol). This feed gas A was previously referred to as the "first" feed gas and will be referred to below as the "first" feed gas. For example, this is essentially pure ethane. For possible ethylene contents of a corresponding first feed gas, please refer to the explanations above. Furthermore, a further feed gas, previously and subsequently referred to as the "second" feed gas, is fed into the reactor. This second feed gas is a gas mixture recirculated from method 400, which contains in particular ethane and hydrocarbons with three and four carbon atoms. Reference is made to the following explanations for the formation of the second feed gas.

The first feed gas A and the second feed gas B are fed into reactor 1 and processed there with steam (not illustrated) by steam cracking. In this way a product mixture C is obtained, which is also known as cracked gas. In addition to products and by-products of steam cracking, the product mixture C also contains unreacted starting materials, in this case especially ethane, as well as water from the added steam. The product mixture C is therefore fed to a processing with the method steps 2 to 4 and a separation referred to with 10 as a whole in to remove the corresponding unwanted components.

The processing initially comprises a water quench for cooling and process steam condensation as well as compression in a typically multi-stage compressor in method step 2. Hydrocarbons with five or more carbon atoms can already be separated from the product mixture C, i.e. components of the so-called pyrolysis gasoline. Corresponding components can be withdrawn from method step 2 in the form of a material stream D. The material stream D is then used for the production of the corresponding components. Sour gas can also be removed. A compressed gas mixture which has been freed of at least some of the hydrocarbons with five carbon atoms and which is now called E can now be fed to a pre-cooling and drying method 3. In the course of this pre-cooling and drying, hydrogenation 4, the so-called raw gas hydrogenation, can also be carried out, in which in particular acetylene is converted to ethylene and mono- and polyunsaturated hydrocarbons with three or more carbon atoms and heavier components are partially converted to less unsaturated components. Hydrogenation can also take place in the separation described below, which would, however, have the disadvantage that in most forms acetylene and hydrocarbons returned to the reactor, which are initially unsaturated and have three and four carbon atoms, must be hydrogenated separately (not described further). A gas mixture F processed in method steps 2 to 4, previously and subsequently referred to as the "subsequent mixture", is fed to separation 10.

In the example shown, separation 10 first comprises a dethanisation step 5', previously and subsequently also referred to as the "first pre-separation step", in which a light fraction H essentially containing ethane, ethylene and lower boiling point compounds and a heavy fraction G essentially containing hydrocarbons containing three or more carbon atoms are formed. The former is subjected to demethanisation 6, previously and subsequently also referred to as the "second pre-separation step", the latter to debutanisation 8, previously and subsequently also referred to as the 'further separation step'.

In the second pre-separation step 6, the light fraction H from the first pre-separation step 5', which, as mentioned above, essentially contains ethane, ethylene and low-boiling compounds, is freed of the low-boiling compounds. In this way, a light fraction I is formed, essentially containing methane and hydrogen, which can be withdrawn from method 100 and/or used, for example, for firing reactor 1. It is also possible to recover hydrogen from a corresponding gas mixture. It should be noted here that in further designs, the sequence of the pre-separation step 5' (or pre-separation steps 5 and 5" in the subsequent examples according to the invention) and pre-separation step 6 can be reversed. A heavy fraction K from the second pre-separation step 6, a gas mixture freed of methane and hydrogen and still containing essentially ethane and ethylene in the 400 method, is subsequently fed to an ethylene separation step 7', which here corresponds to a classical C2 separation, where a light fraction L containing essentially ethylene and a heavy fraction M containing essentially ethane are formed. The former can be delivered in the form of a material stream L to the plant boundary illustrated by the arrow symbol, the latter is used in the form of a material stream M to form the second feed gas B. The latter is used in the form of a material stream M for the formation of the second feed gas B.

In further separation step 8, the heavy fraction G from the first pre-separation step is converted into a light fraction N, which essentially contains hydrocarbons with three and four (and possibly five, see above explanations) carbon atoms, and a heavy fraction O, which essentially contains hydrocarbons with five and possibly more carbon atoms. The former is combined with the heavy fraction M from the ethylene separation step and is thus used to form the second feed gas B. The latter is then used for the production of the second feed gas B. The ethylene is then separated from the ethylene. The heavy fraction O from the further separation step 8 is combined with the material flow D and carried out in the form of a pyrolysis gasoline flow P. The separation of the heavy fraction O from the further separation step 8 is carried out in the form of a pyrolysis gasoline flow P. The separation of the heavy fraction O from the further separation step 8 is carried out in the form of a pyrolysis gasoline flow P.

As mentioned above, in the method illustrated in FIG. 1, 400, a complete separation of hydrocarbons with three and four carbon atoms from ethane is carried out, which in itself is superfluous. In particular, the deethanisation 5 method involves a superfluous separation effort. The present invention therefore proposes a method in various forms in which a corresponding separation effort is reduced.

Figure 2:
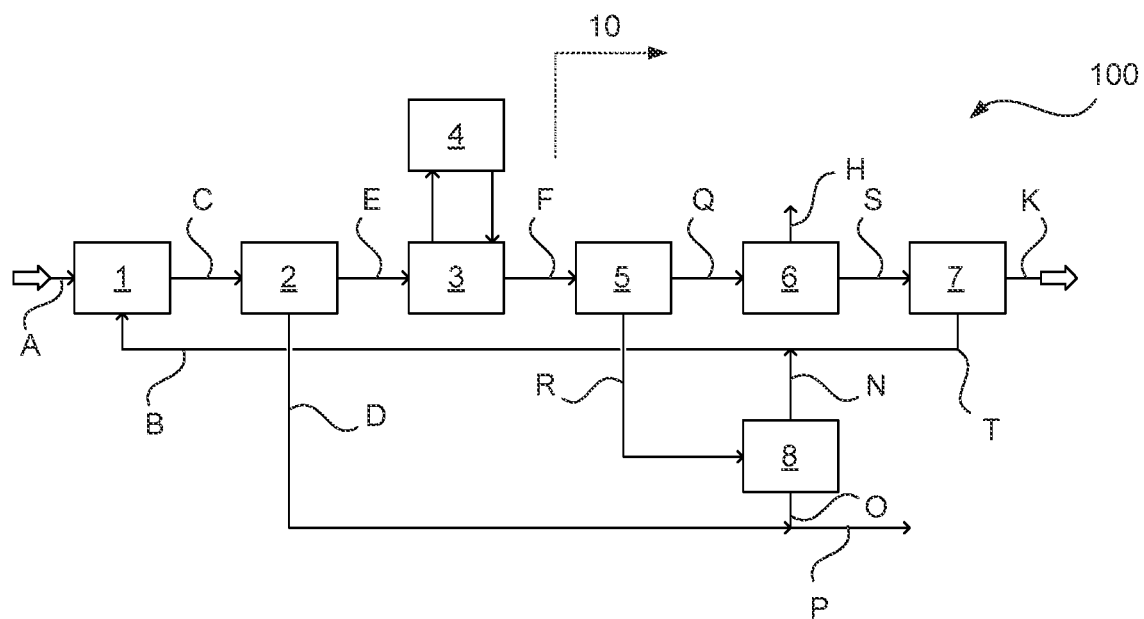
FIG. 2 illustrates a procedure according to an embodiment of the invention.

FIG. 2 illustrates a procedure according to an embodiment of the present invention and designates a total of 100. This design corresponds to the "first alternative" mentioned several times above.

Method 100 as shown in FIG. 2 does not necessarily differ from non-inventive method 400, which is shown in FIG. 1, with respect to steps 1 to 4. With regard to these procedural steps, reference is therefore made to the above explanations. In procedure 100 according to FIG. 2, however, a dethanization deviating from procedure 400 according to FIG. 1 is carried out as the first separation step, which is therefore referred to here as differently by 5. In contrast to a gas mixture essentially containing ethane, ethylene and lighter components (cf. light fraction H in FIG. 1) on the one hand and a gas mixture essentially containing hydrocarbons with three or more carbon atoms on the other hand (cf. light fraction G as shown in FIG. 1), a light fraction Q is formed which, in addition to ethane, ethylene and lighter components, also contains a portion of the hydrocarbons with three carbon atoms from the subsequent mixture F added in the first pre-separation step 5, and a heavy fraction R which contains only a portion of the hydrocarbons with three carbon atoms and otherwise the heavier hydrocarbons from the subsequent mixture F and optionally ethane. The light fraction Q is essentially free of hydrocarbons with four or more carbon atoms. Conversely, the heavy fraction R fraction drawn off is poor in or free of ethylene and lighter boiling components.

Here, too, the light fraction Q is fed to the second pre-separation step 6, in which a light fraction H, essentially containing methane and hydrogen, is formed. However, in contrast to the heavy fraction K from the second pre-separation step 6 of method 400 according to FIG. 1, a remaining heavy fraction S also contains hydrocarbons with three carbon atoms in addition to ethane and ethylene. It is fed to an ethylene separation step 7. In contrast to the ethylene separation step "7" of method 400 according to FIG. 1, a light fraction K essentially containing ethylene is also formed here, but a gas mixture consisting essentially of ethane and hydrocarbons with three carbon atoms remains as the heavy fraction T. The gas mixture is then separated from the ethylene in the 7" separation step of method 400 according to FIG. 1. This can occur in particular in the bottom of a rectification column used in ethylene separation step 7. The heavy fraction T from the ethylene separation step 7 is used in the illustrated manner in the formation of the second feed gas B. The fraction T is the same as the fraction T from the ethylene separation step 7.

The further separation step 8 according to method 100 essentially corresponds to separation step 8 according to method 400 according to FIG. 1, wherein, however, only those hydrocarbons with three carbon atoms which have not already passed through the light fraction Q and from the first pre-separation step 5 and the heavy fraction S from the second pre-separation step 6 into the heavy fraction T from the ethylene separation step 7 pass into the light fraction N of the further separation step 8.

Figure 3:
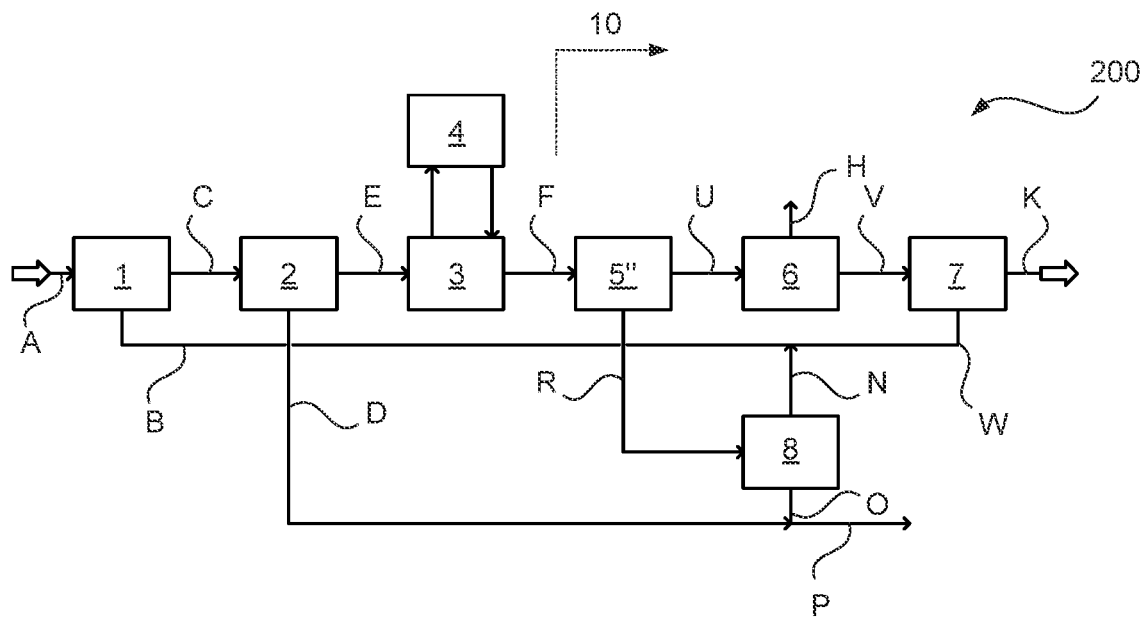
FIG. 3 illustrates a procedure according to an embodiment of the invention.

FIG. 3 illustrates a procedure according to a further form of the present invention and is designated 200 as a whole. Method 200 corresponds to the "second alternative" mentioned several times before. It differs from method 100 according to FIG. 2 essentially in the different execution of the first pre-separation step 5. The first pre-separation step 5 is therefore designated 5" in procedure 200 according to FIG. 3.

In contrast to the first pre-separation step 5 of method 100, in the first pre-separation step 5" of method 200 a light fraction U is formed which, in addition to ethane, ethylene and the lighter-boiling components, contains not only a part of the hydrocarbons with three carbon atoms but also a part of the hydrocarbons with four carbon atoms from the subsequent mixture F. The first pre-separation step 5" of method 200 is a light fraction U which, in addition to ethane, ethylene and the lighter-boiling components, contains not only a part of the hydrocarbons with three carbon atoms but also a part of the hydrocarbons with four carbon atoms from the subsequent mixture F. This is led to the second pre-separation step 6. While a light fraction H formed in the second pre-separation step 6 also contains methane and hydrogen predominantly or exclusively, the remaining heavy fraction V contains ethane, ethylene and hydrocarbons with three and four carbon atoms. In the ethylene separation step, which is designated 7 here as before, a light fraction K essentially containing ethylene and a heavy fraction W essentially containing ethane, hydrocarbons with three and hydrocarbons with four carbon atoms are formed.

A heavy fraction R formed in the first pre-separation step 5" does not contain the hydrocarbons with three and four carbon atoms passing through fractions U and V into fraction W, so that these do not pass into the light fraction N of further separation step 8.

Figure 4:
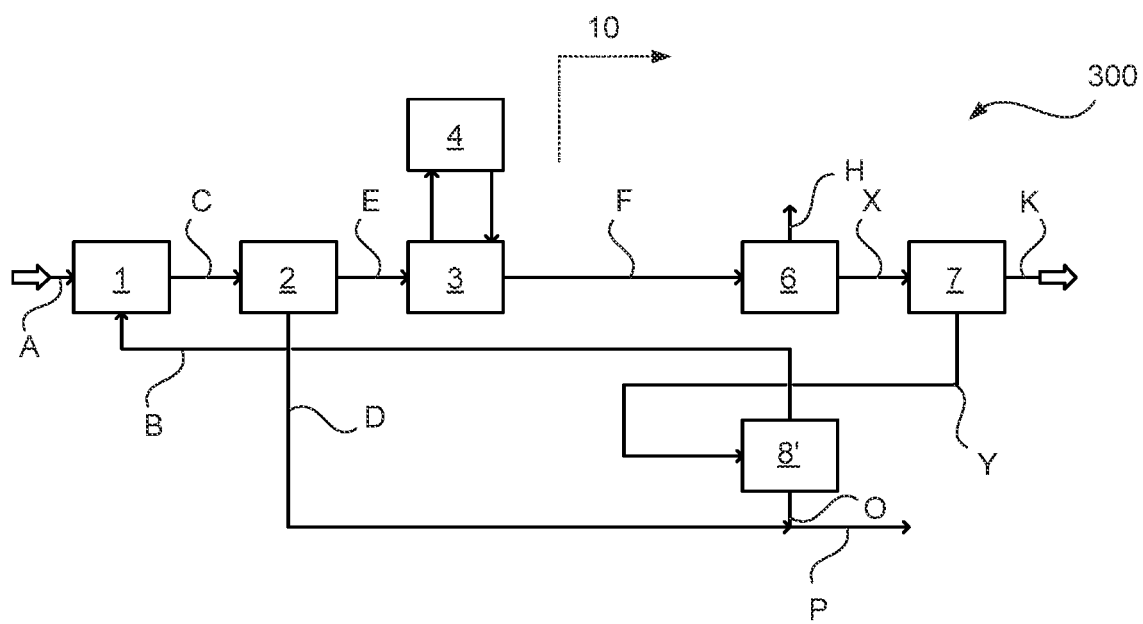
FIG. 4 illustrates a procedure according to an embodiment of the invention.

FIG. 4 illustrates another embodiment of the present invention, which is designated 300 in total. Method 300 corresponds to the "second alternative" mentioned several times before. As illustrated by method 300 in FIG. 4, a first pre-separation step 5', 5 or 5" (see previous FIGS. 1 to 3) can also be omitted completely in a design in accordance with the invention. In this case, the entire material flow F, i.e. the subsequent mixture described, is fed to demethanization 6, i.e. a single pre-separation step. A heavy fraction X obtained here contains not only ethane and ethylene but also hydrocarbons with three, four and at least five carbon atoms. This fraction X is fed to ethylene separation step 7, in which the light fraction K containing mainly or exclusively ethylene can also be formed and removed. A remaining heavy fraction Y can be fed to a further separation step, which can be similar to the separation step 8 according to the present figures and is therefore marked 8'. The light fraction formed in this 8' separation step contains ethane and hydrocarbons with three and four (and possibly five) carbon atoms. It is therefore used directly as the second feed gas B. The composition of the heavy fraction O does not differ from that of the invention as described above.

The invention claimed is:

1. A method for the production of ethylene, in which a first feed gas (A) and a second feed gas (B) are fed to a reactor (1) and processed therein by steam cracking to obtain a product mixture (C), the first feed gas (A) comprising more than 90% by weight of saturated hydrocarbons and more than 80% by weight of ethane, and wherein the product mixture (C) or a part thereof is subjected to a treatment (2, 3, 4) to obtain a subsequent mixture (F) containing hydrogen, methane, ethane, ethylene and hydrocarbons having three, four and at least five carbon atoms, and the subsequent mixture (F) or a part thereof is subjected to a separation (10), characterized in that the separation (10) comprises an ethylene separation step (7), to which at least the ethane, the ethylene and the hydrocarbons having three carbon atoms from the subsequent mixture (F) or a part thereof are fed in a common separation feed (S, V, X) unseparated from one another, wherein in the ethylene separation step (7) a light fraction (K) containing more than 95 mole percent of ethylene and a heavy fraction (T, W, Y) containing at least a portion of the ethane from the common separation feed (S, V, X) and at least 15% by weight of the hydrocarbons having three and four carbon atoms from the common separation feed (S, V, X) are formed, and wherein the heavy fraction (T, W, Y) from the ethylene separation step (7) or a portion thereof is used as part of or to form the second feed gas (B).

2. The method according to claim 1, in which the separation feed (S, V) supplied to the ethylene separation step (7) is formed using a first pre-separation step (5, 5") and a second pre-separation step (6), the first pre-separation step (5, 5") being supplied with the subsequent mixture (F) or its part subjected to separation (10) in unchanged composition, a light fraction (Q, U) and a heavy fraction (R) being formed in the first pre-separation step (5, 5"), wherein the light fraction (Q, U) from the first pre-separation step (5, 5") or a part thereof is fed to the second pre-separation step (6), wherein in the second pre-separation step (6) a light fraction (H) and a heavy fraction (S, V) are formed, and wherein the heavy fraction (S, V) from the second pre-separation step (6) or a part thereof is used as the separation feed (S, V) or as a part of the separation feed (S, V) fed to the ethylene separation step (7).

3. The method according to claim 2, in which the light fraction (Q) from the first pre-separation step (5) contains a total of less than 1 mole percent of hydrocarbons having four and at least five carbon atoms and in the remainder methane, ethane, ethylene and hydrocarbons having three carbon atoms, and in which the heavy fraction (R) from the first pre-separation step (5) contains a total of less than 1 mol % of hydrogen, methane and ethylene and in the remainder ethane, hydrocarbons having three, four and at least five carbon atoms.

4. The method according to claim 3, wherein the light fraction (H) from the second pre-separation step (6) contains more than 99 mole percent of methane and hydrogen in total and the heavy fraction from the second pre-separation step (6) contains less than 1 mole percent of methane and hydrogen in total and in the remainder ethane, ethylene and hydrocarbons having three carbon atoms.

5. The method according to claim 3, further comprising subjecting the heavy fraction (S, V) from the first pre-separation step (5, 5") or a portion thereof to a further separation step (8) in which a light fraction (N) and a heavy fraction (O) are formed, the light fraction containing either less than 1 mole percent of hydrocarbons having at least six carbon atoms and in the remainder hydrocarbons having three, four and five carbon atoms or less than 1 mole percent of hydrocarbons having at least five carbon atoms and in the remainder hydrocarbons having three and four carbon atoms.

6. The method according to claim 5, wherein the light fraction (N, B) from the further separation step (8) or a part thereof is used to form the second feed gas (B).

7. The method according to claim 6, wherein the heavy fraction (O) from the further separation step (8, 8') is carried out from the process (100, 200, 300) together with a fraction (D) from the treatment (2) containing hydrocarbons having at least five or at least six carbon atoms.

8. The method according to claim 5, wherein the heavy fraction (O) from the further separation step (8, 8') is carried out from the process (100, 200, 300) together with a fraction (D) from the treatment (2) containing hydrocarbons having at least five or at least six carbon atoms.

9. The method according to claim 2, wherein the light fraction (U) from the first pre-separation step (5") contains a total of less than 1 mole percent of hydrocarbons having at least five carbon atoms and in the remainder methane, ethane, ethylene and hydrocarbons having three and four carbon atoms, and wherein the heavy fraction (R) from the first pre-separation step (5) contains a total of less than 1 mole percent of hydrogen, methane and ethylene and in the remainder ethane and hydrocarbons having three, four and at least five carbon atoms.

10. The method according to claim 9, wherein the light fraction (H) from the second pre-separation step (6) contains a total of more than 99 mole percent methane and hydrogen and the heavy fraction from the second pre-separation step (6) contains a total of less than 1 mole percent methane and hydrogen and in the remainder ethane, ethylene and hydrocarbons having three and four carbon atoms.

11. The method according to claim 9, further comprising subjecting the heavy fraction (S, V) from the first pre-separation step (5, 5") or a portion thereof to a further separation step (8) in which a light fraction (N) and a heavy fraction (O) are formed, the light fraction containing either less than 1 mole percent of hydrocarbons having at least six carbon atoms and in the remainder hydrocarbons having three, four and five carbon atoms or less than 1 mole percent of hydrocarbons having at least five carbon atoms and in the remainder hydrocarbons having three and four carbon atoms.

12. The method according to claim 1, in which the separation feed (X) supplied to the ethylene separation step (7) is formed by using a single pre-separation step (6) to which the subsequent mixture (F) is supplied in unchanged composition and in which a light fraction (H) containing in total more than 99 mole percent methane and hydrogen and a heavy fraction (X), containing in total less than 1 mole percent methane and hydrogen and the balance ethane, ethylene and hydrocarbons having three, four and at least five carbon atoms, wherein the heavy fraction (X) from the single pre-separation step (6) or a part thereof is used as the separation feed (X) or as a part of the separation feed (X) fed to the ethylene separation step (7).

13. The method according to claim 12, in which at least a portion of the heavy fraction (X) from the only pre-separation step (6) remaining after the ethylene separation step (7) is fed to a further separation step (8') in which a light fraction (B) and a heavy fraction (O) are formed, wherein the light fraction contains either less than 1 mole percent of hydrocarbons having at least six carbon atoms and in the remainder hydrocarbons having three, four and five carbon atoms or less than 1 mole percent of hydrocarbons having at least five carbon atoms and in the remainder hydrocarbons having three and four carbon atoms.

14. The method according to claim 13, wherein the light fraction (N, B) from the further separation step (8) or a part thereof is used to form the second feed gas (B).

15. The method according to claim 13, wherein the heavy fraction (O) from the further separation step (8, 8') is carried out from the process (100, 200, 300) together with a fraction (D) from the treatment (2) containing hydrocarbons having at least five or at least six carbon atoms.

\* \* \* \* \*